United States Patent [19]

Megerle

[11] Patent Number: 5,874,046

[45] Date of Patent: *Feb. 23, 1999

[54] BIOLOGICAL WARFARE AGENT SENSOR SYSTEM EMPLOYING RUTHENIUM-TERMINATED OLIGONUCLEOTIDES COMPLEMENTARY TO TARGET LIVE AGENT DNA SEQUENCES

[75] Inventor: Clifford A. Megerle, Thousand Oaks, Calif.

[73] Assignee: Raytheon Company, El Segundo, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 740,539

[22] Filed: Oct. 30, 1996

[51] Int. Cl.$^6$ .................. G01N 27/30; G01N 27/327; G01N 27/406

[52] U.S. Cl. .................. 422/68.1; 422/50; 422/62; 422/63; 422/67; 422/69; 422/82.01; 422/82.02; 436/501; 435/6; 435/29; 435/30; 435/40.5; 435/283.1; 435/285.1; 435/285.2; 435/287.1; 435/287.2; 435/287.3; 435/289.1; 935/77; 935/78; 935/88

[58] Field of Search .................. 435/4, 6, 29, 30, 435/40.5, 173.1, 283.1, 285.1, 285.2, 287.1–287.3, 289.1; 436/501; 422/50, 62, 63, 67, 68.1, 69, 82.01, 82.02

[56] References Cited

U.S. PATENT DOCUMENTS

| | | | |
|---|---|---|---|
| 4,840,893 | 6/1989 | Hill et al. | 435/6 |
| 5,591,578 | 1/1997 | Meade et al. | 435/6 |
| 5,632,957 | 5/1997 | Heller et al. | 422/68.1 |

FOREIGN PATENT DOCUMENTS

WO 95/15971   6/1995   WIPO .

OTHER PUBLICATIONS

T.J. Meade et al, "Electron Transfer through DNA: Site–Specific Modification of Duplex DNA with Ruthenium Donors and Acceptors", *Angewandte Chemie,* International Edition in English, vol. 34, No. 3, pp. 352–354 (Feb. 21, 1995).

*Primary Examiner*—Ardin H. Marschel
*Attorney, Agent, or Firm*—Colin M. Raufer; Leonard A. Alkov; Glenn H. Lenzen, Jr.

[57] ABSTRACT

A sensor system and method are provided that are capable of the real-time detection of target live microorganisms, such as biological warfare agents. The sensor system includes a highly-sensitive, highly-selective sensor cell that comprises a single-stranded oligonucleic acid sequence that is complementary to a portion of the DNA of a target live microorganism, the oligonucleic acid having been modified with the covalent attachment of electron donor and acceptor moieties. In the presence of the targeted microorganism, hybridization occurs between the modified oligonucleic acid and the microorganism's DNA, such that the electron conductance between the electron transfer moieties greatly increases, thereby providing a means of detecting the presence of the target live microorganism. Aside from the sensor cell, the sensor system also includes an inlet port in the sensor cell wall by which to introduce a sample from the fluid environment into the sensor cell; a cell wall disrupter to release the nucleic acid of the fluid sample into the sensor cell; an electron transfer rate measuring system to gauge the electron transfer rate between the electron transfer moieties of the modified oligonucleic acid; a power source; a microcontroller to analyze the measured electron transfer rate for evidence of hybridization; and a communication system for relaying information regarding the presence or absence of the target live microorganism to the user of the sensor system. It is contemplated that the sensor system, exclusive of a battery and pump pack, will be only slightly larger than a pack of cigarettes and light enough to be comfortably worn and carried by personnel.

13 Claims, 2 Drawing Sheets

BIOLOGICAL WARFARE AGENT SENSOR SYSTEM EMPLOYING RUTHENIUM-TERMINATED OLIGONUCLEOTIDES COMPLEMENTARY TO TARGET LIVE AGENT DNA SEQUENCES

BACKGROUND OF THE INVENTION

1. Field of the Invention

The present invention relates generally to sensors for specific nucleic acid sequences. More particularly, the present invention relates to a real-time sensor system for the detection of target live agent deoxyribonucleic acid, such as would be useful in the detection of biological warfare agents.

2. Description of Related Art

The detection of bacteria and viruses that pose a threat to human populations is an invaluable capability. With early detection of a harmful microorganism, persons located in the vicinity of an infected area may be notified so that they might take necessary precautions for their protection, such as fleeing to a safe haven, consuming appropriate antibiotics, or donning protective gear.

While the proliferation of harmful air-borne or water-borne microorganisms in an area might be a natural occurrence or, at least, an unintended result of human interference (e.g., the contamination of bodies of water by raw sewage), the potential for rogue governments and terrorists to employ biological warfare agents (BWA's) against troops and civilian populations is an increasing concern that makes the need for sensor systems for harmful microorganisms all the more urgent. The sheer variety of BWA's that might be employed requires that a sensor system should be highly sensitive and highly selective with regard to target live agents. Examples of potential BWA's include anthrax, typhoid fever, smallpox, and valley fever. Given the speed with which BWA's might adversely affect a population, it would be highly desirable that the sensor system offer real-time detection.

There are available methods by which harmful microorganisms might be detected, such as antibody-based techniques and gene-probe assays. However, antibody-based techniques suffer from poor specificity and are not adaptable to field applications. Gene-probe assays have been considered a better alternative to antibody-based techniques alone, but gene-probe assays have been known to require numerous time-consuming steps which are difficult to automate. Neither antibody-based techniques nor traditional gene-probe assays offer the real-time sensor capabilities and the specificities needed to detect harmful microorganisms such as BWA's.

Recently, techniques have been developed which enable the highly specific and sensitive detection of live agents by addressing the genetic material of the biological warfare agent itself. These techniques are disclosed in (1) a patent application having International Publication Number WO 95/15971 (entitled "Nucleic Acid Mediated Electron Transfer"), naming Thomas J. Meade and Jon F. Kayyem as inventors and having been assigned on its face to California Institute of Technology; and (2) a publication entitled "Electron Transfer through DNA: Site-Specific Modification of Duplex DNA with Ruthenium Donors and Acceptors" (*Angew. Chem. Int. Ed. Engl.*, Vol. 34, No. 3, pp. 352–354 (1995)), written by Thomas J. Meade and Jon F. Kayyem.

The method developed by Meade and Kayyem (hereinafter Meade et al) provides for the site-selective modification of nucleic acids with redox active moieties such as transition metal complexes. Specifically, Meade et al demonstrate the placement of ruthenium-containing electron donor and electron acceptor groups onto the ribose backbone of a single strand of DNA, allowing the placement of a ruthenium atom at or near each end of a single strand of DNA. The significance of this feat lies in the electrical conductance differential between ruthenium-doped single strands of DNA compared to that of a double helix comprising one such single strand and a non-doped complementary strand. In general, a double strand of polynucleotide is about one million times more electrically conductive than a single strand. When a ruthenium-doped single strand is combined with its non-doped complementary strand, one of the ruthenium-containing groups serves as an electron source and the other as an electron sink, such that electrons flow back and forth between these two groups. Thus, the double helix creates a highly conductive path along its molecular axis between the electron donor and the electron acceptor that does not exist in a single strand of DNA. In addition to serving as electrical connectors into and out of the molecule, ruthenium atoms have the added virtue of neither disrupting nor distorting the overall shape of the DNA backbone.

Prior to the method of Meade et al, the long range transference of electrons in a DNA matrix was hindered by such factors as (1) the random distribution and mobility of the electron donor and the electron acceptor pairs; (2) the potential short distances between the donor and acceptor; and (3) the loose and reversible association of donors and acceptors. Meade et al overcome these obstacles by teaching a method directed to the modification of nucleic acids with electron transfer moieties covalently attached to specific sites of nucleic acids on a single strand of DNA in a way that creates no stearic hindrance to hybridization to form a duplexed strand pair. The resulting doped DNA strand is capable of hybridizing to a complementary target sequence in a single stranded nucleic acid and thereafter rapidly transferring electrons between the donor and acceptor.

The method of Meade et al specifically involves the synthesis of two sets of complementary oligonucleotide strands modified first with a terminal aminoribose and then covalently modified with electron donor and acceptor moieties, such as redoxactive ruthenium complexes. Since the ruthenium complexes will react with the heterocyclic nitrogen atoms of the bases, the bases are protected by employing an unmodified complementary strand as a large hydrogen-bonded blocking group. After reaction with the ruthenium complex, the complementary strand is removed and the modified oligonucleotide is purified in accordance with known procedures.

By employing the methods of Meade et al, one may discriminate between DNA strands that are identical to the original and those that differ by, for example, one base pair out of fifteen pairs (i.e. a match of 14 of the 15 base pairs in a strand), or by more than one base pair, by observing the electrical conductivity of an oligonucleotide. Meade et al have thus developed an electrical method of distinguishing between different sequences of DNA. Meade et al expressly contemplate employing their method of DNA strand detection in the creation of bioconductors and diagnostic probes, such as for medical applications.

A need remains for a real-time sensor system for harmful microorganisms that offers highly sensitive and highly selective characteristics; that may be employed for environmental sampling in the field, such as air and water sampling; and that is capable of alerting both those in its immediate vicinity as well as those at remote locations of the presence and type of microorganisms detected. Further, the sensor should be conveniently sized for use in the field and should be relatively inexpensive to produce and operate.

SUMMARY OF THE INVENTION

In accordance with the present invention, a sensor system and method are provided that are capable of detecting in real-time the presence of target live microorganisms in a fluid environment, whether air or liquid. Further, a method for making such a sensor system is provided. The sensor system includes a highly-sensitive, highly-selective sensor cell that detects the target live microorganism by matching the sequence of bases in a portion of the microorganism's DNA to that of a synthesized complementary sequence contained within the sensor cell, which is a virtually interference-free method of identification. The synthesis of the complementary sequence may be accomplished such as by the above-described techniques disclosed by Meade et al. The sensor system comprises:

(a) a sensor cell comprising:
  (i) at least one electrode, and
  (ii) at least one single-stranded oligonucleic acid in electrical communication with at least one electrode, the single-stranded oligonucleic acid being complementary to the sequence of nucleotides in a portion of the target agent's DNA or RNA and therefore capable of hybridizing therewith to form a hybridization complex, the single-stranded oligonucleic acid containing at least one electron donor moiety and at least one electron acceptor moiety, the electron donor moiety and the electron acceptor moiety being covalently attached to the single-stranded oligonucleic acid;

(b) at least one inlet port to the sensor cell, with the inlet port allowing fluidic communication between the fluid environment surrounding the sensor unit and the internal volume of the sensor cell, such that fluid (either liquid or air) from the fluid environment may be imported into the sensor cell, with the fluid including cells having cell walls encapsulating DNA and/or RNA;

(c) a cell wall disrupter to lyse the cell walls such that the encapsulated DNA and/or RNA is released into the sensor cell;

(d) an electron transfer rate measuring system for determining the electron transfer rate through the single-stranded oligonucleic acid having attached electron donor and/or electron acceptor moieties, the single-stranded oligonucleic acid exhibiting a base electron transfer rate in the absence of the target sequence of nucleotides and an increased electron transfer rate in the presence of the target sequence, having formed a hybridization complex;

(e) a power source to supply the power for operation of said sensor system;

(f) a microcontroller to compare the measured electron transfer rate with the base electron transfer rate to determine the presence or absence of the target sequence of nucleotides in the fluid sample; and (g) a communication system for relaying information regarding the presence or absence of the target sequence of nucleotides in the fluid to a user of the sensor system.

A sensor made in accordance with the present invention will alert the user to the presence of the target live microorganisms, thereby enabling the user to take protective actions such as withdrawing from the infected area, consuming appropriate antibiotics, and/or donning personal protective gear. For example, it is contemplated that the present sensor is particularly well-suited for use by troops, or in unattended ground sensors or in manned or unmanned ground vehicles or aircraft, to detect the presence of BWA's. Notably, if the present sensor system is linked to a communication network, it may be used to alert remote personnel to the threat of BWA's (such as battlefield command and control personnel) and to relay to remote personnel the location and type of BWA's present, such as by tandem use of a digital radio link and a global positioning satellite receiver. A field commander so alerted would then be able to adjust his tactics knowing the location and extent of the biological agent threat on the battlefield.

It is contemplated that a sensor system made in accordance with the invention will be only slightly larger than a pack of cigarettes and light enough to be comfortably worn and carried by personnel without difficulty throughout their daily activities, or to be mounted in very small ground sensors vehicles, or aircraft. It incorporates very low-cost technology and will have a field replaceable, disposable sensor cell.

DESCRIPTION OF THE PREFERRED EMBODIMENTS

Figure 1:
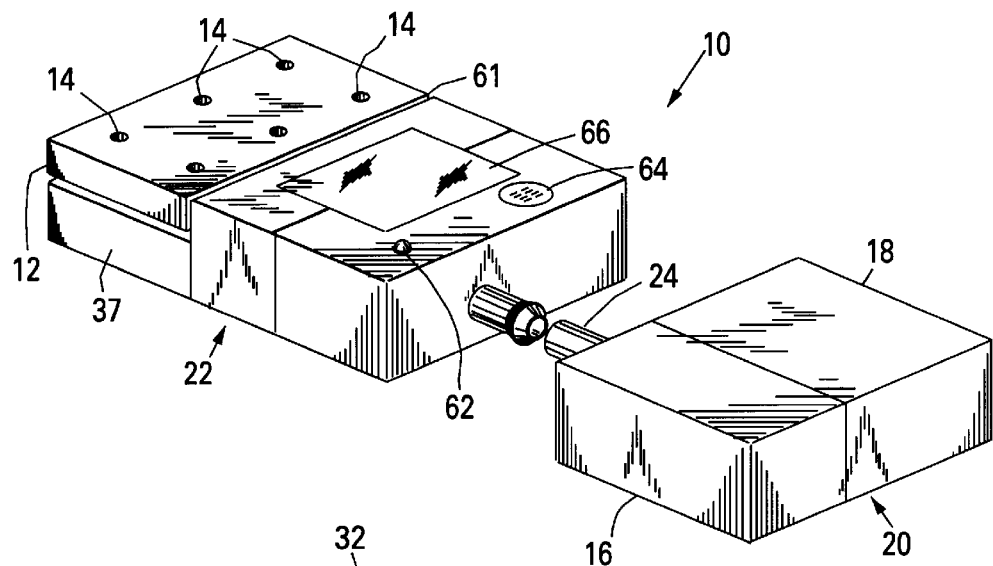
FIG. 1 illustrates a sensor unit assembled in accordance with the invention.

A sensor system is provided herein to detect airborne and waterborne target live microorganisms in real time. The sensor system offers highly specific and highly sensitive detection abilities using such techniques as developed by Thomas J. Meade and Jon F. Kayyem (hereinafter "Meade et al") and disclosed in the following two references: (1) a patent application having International Publication Number WO 95/15971 (entitled "Nucleic Acid Mediated Electron Transfer"), naming Thomas J. Meade and Jon F. Kayyem as inventors and having been assigned on its face to California Institute of Technology; and (2) a publication entitled "Electron Transfer through DNA: Site-Specific Modification of Duplex DNA with Ruthenium Donors and Acceptors" (*Angewandte Chemie—International Edition in English*, 34(3), pp. 352–354 (1995)), written by Thomas J. Meade and Jon F. Kayyem.

In short, Meade et al teach a method by which an oligonucleic sequence may be synthesized that is complementary to that of a targeted live microorganism and that has covalently attached electron acceptor and donor moieties at or near opposing ends of the sequence. The electron conductance of a single strand of such a doped oligonucleic sequence is roughly 100 electrons per second while, in comparison, a double helix exhibits an electrical conductance of about 1,000,000 electrons per second, or a 10,000-fold increase. When a ruthenium-doped single strand is combined with its non-doped complementary strand, one of the ruthenium-containing groups serves as an electron source and the other as an electron sink, such that electrons flow back and forth between these two groups. Thus, the double helix creates a highly conductive path along its molecular axis between the electron donor and the electron acceptor that does not exist in a single strand of DNA. The present sensor system employs this technology to detect target live microorganisms: a doped oligonucleic sequence is attached to an electrode in the sensor system and its electrical conductance is systematically measured. An electron conductance increase by several orders of magnitude indicates that the doped oligonucleic acid has hybridized with a complementary strand and that the target live microorganism is within the vicinity of the sensor system. While the present sensor system is not limited to the method by which Meade et al achieve a synthesized oligonucleic acid terminated with electron acceptor and donor moieties, no other method is presently known by which such site-selective modification of oligonucleic sequences may be achieved.

At the outset, it is noted that unless otherwise stated, the terms "nucleic acid" or "oligonucleotid" or grammatical equivalents thereof herein means at least two nucleotides covalently linked together. A nucleic acid employed in the present sensor system will generally contain phosphodiester bonds, although in some cases a nucleic acid may have an analogous backbone comprising, for example, phosphoramide, phosphorothioate, phosphorodithioate, O-methylphos-phoroamideite linkages, or peptide nucleic acid linkages, as described in Meade et al, '971. The nucleic acids may be single stranded or double stranded, as specified. The nucleic acid may be DNA, RNA, or a hybrid, where the nucleic acid contains any combination of deoxyribo- and ribonucleotides, and any combination of uracil, adenine, thymine, cytosine, and guanine. In some instances, e.g., in the case of an "intervening nucleic acid", the term nucleic acid refers to one or more nucleotides.

The terms "electron donor moiety", "electron acceptor moiety", and "electron transfer moieties" or grammatical equivalents thereof herein refer to molecules capable of electron transfer under certain conditions. It will be understood by those of ordinary skill in the art that electron donor and acceptor capabilities are relative; i.e., a molecule which can lose an electron under certain experimental conditions may be able to accept an electron under different experimental conditions. Generally, electron transfer moieties contain transition metals, such as ruthenium, as components, but the invention is not so limited.

The term "target sequence" or grammatical equivalents thereof herein means a nucleic acid sequence on a single strand of nucleic acid. The target sequence may be a portion of a gene, regulatory sequence, genomic DNA, MRNA, or others. It will be understood by those having ordinary skill in the art that longer target sequences are more specific.

Turning now to FIG. 1, one embodiment of a sensor system 10 constructed in accordance with the invention is depicted. The single strands of oligonucleotide sequences modified with electron donor and acceptor moieties, such as by the method of Meade et al, are contained in the sensor cell 12 as connected to an electrode (internal to the sensor cell 12 and therefore not shown in FIG. 1). As depicted in FIG. 1, the sensor cell 12 is in the form of a replaceable cartridge, although the sensor cell could also be a permanent fixture of the sensor system 10. It would be advantageous for the sensor cell 12 to be disposable: the useful life of a sensor cell is a single detection of a target live microorganism, although the remaining parts of the sensor system 10 remain in working order.

Samples of the surrounding air or water are imported into the sensor cell 12 for testing via inlet ports 14. In the embodiment of FIG. 1, a pump 16 and associated power source 18, which is preferably a battery, are contained in a separate pack 20 and connected to the main body 22 of the sensor system 10 by an integral air tube/power cable connection 24 (The locations of the pump and power source are indicated in FIG. 1 as within pack 20; FIG. 1 does not actually depict the pump and power source.). For example, while the sensor body 22 might be strapped onto one's chest external to clothing and gear such that the inlet ports 14 of the sensor body remain unimpeded, a separate battery pack and pump system 20 might be attached to one's belt and connected to the sensor body via the necessary air tubes and wires 24. Alternatively, pump 16 and power source 18 may also be incorporated internal to the main body 22 of the sensor system 10.

Thus, it is contemplated that a fluid sample of the environment surrounding the sensor unit 10 is introduced into the sensor cell 12 by the combination of a miniaturized pump 16 and air inlet ports 14. The pump 16 provides the suction necessary for samples of the surrounding air or water to flow into the sensor cell 12 through the inlet ports 14, although a liquid sample may be manually introduced by a dropper or other means, albeit less conveniently than with a pump 16. The type of pump 16 employed in the practice of the invention is not limited to any particular type, with the only requirement being sufficient compactness for use in the sensor unit 10. Examples of suitable types of pumps include, but are not limited to, rotary vane pumps, bellows pumps, cyclones, and fans.

In the case of air sampling, a micromachined silicon microfluidic device is preferably employed. Specifically, a miniaturized version of the SpinCon® micro-cyclone air sampler, developed by Midwest Research Institute, is contemplated. This device samples air and concentrates suspended particles into a liquid. In the case of liquid sampling, it is contemplated that an appropriate miniature pump 16 will be used in conjunction with inlet ports 14 to draw liquids into the sensor cell 12. It is noted that, in the case of liquid sampling, one would necessarily admix some concentrated ionic mother liquor with the sample to render it an electrolyte which would then be introduced into the sensor cell 12.

The electrical conductance through the modified oligonucleic sequence affixed to the electrode in the sensor cell 12 is measured by a means contained internal to the main body 22 of the sensor system. The measurement of electrical conductance may be accomplished using equipment and techniques well-known in the art. Any method of measuring electron conductance that is accurate and compatible with other components in the sensor system may be employed to measure the conductivity through the oligonucleotides, although preferably the electrical conductance is measured by electrochemical means in conjunction with cyclic voltammetry, pulse polarography, and/or impedance measurements, which are well-known and can be implemented in miniaturized electronics. Most preferably, cyclic voltammetry is employed in the practice of the invention.

Figure 2:
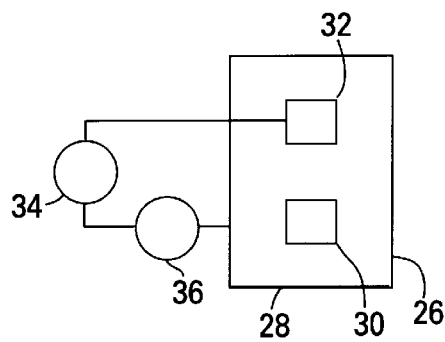
FIG. 2 is a schematic of an embodiment of the analog electronics and electrochemical power supply of the sensor unit.

The schematic of FIG. 2 illustrates a preferred embodiment in which the electrical conductance is measured electrochemically. In that embodiment, an electrolyte chamber 26 is provided filled with a gelled electrolyte 28, and the detector electrode 30 and reference electrode 32 are placed therein, with the substituted oligonucleotide attached by one end to the detector electrode 30. Thus, in this embodiment, one end of the oligonucleotide is free in the electrolyte, while the other is bound to the electrode 30. A voltage source 34 is provided that can either be cycled or pulsed, and the current is measured by equipment 36, such as an electrometer or electrometer circuit, using well-known techniques. In the embodiment of FIG. 1, the means of measuring the electrical conductance, together with the necessary analogue electronic components, are housed adjacent to the sensor cell in component body 37.

Figure 3:
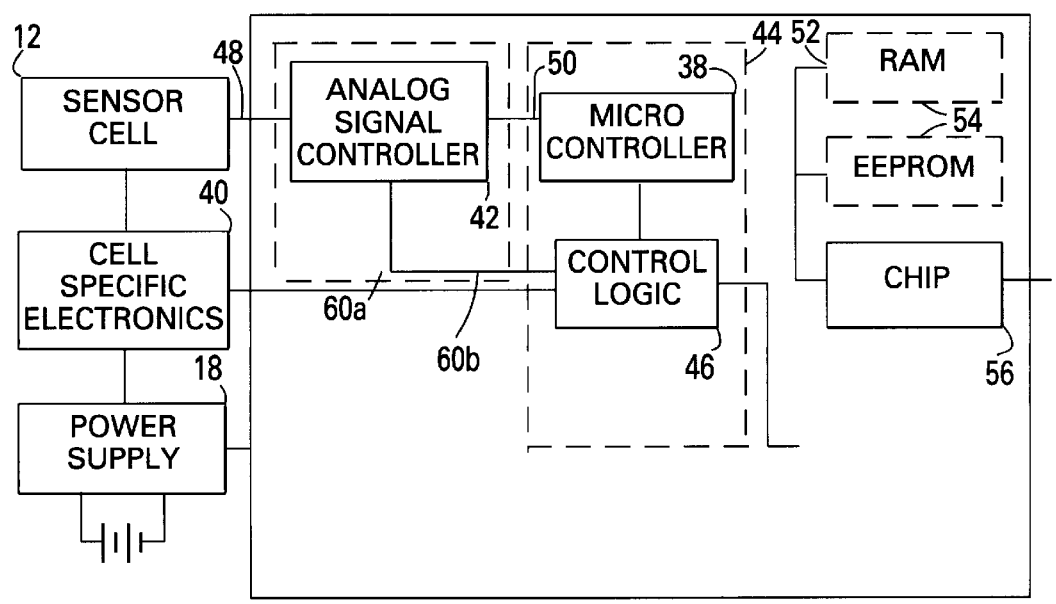
FIG. 3 is a schematic of the contemplated integrated system design for the sensor unit.

It is contemplated that the sensor system 10 will contain a microcontroller 38, as schematically illustrated in FIG. 3, that is capable of receiving data from the electrode(s) 30 in the sensor cell 12 as well as controlling to which electrode 30 in a plurality of sensor cells 12 the signal voltage is directed. Specifically, it is contemplated that the microcontoller 38 receives data either directly from the electrode 30 through an analogue I/O port or through an intermediate analogue application specific integrated circuit ("ASIC") with an A/D converter. The microcontroller 38 would then be employed to reduce the data and form a signal that could be communicated by the sensor unit 10.

Referring to FIG. 3, the electronics schematic of a preferred sensor system 10 is presented therein which includes four major sections: the sensor cell 12 and cell specific electronics 40 (including equipment to detect current changes as well as equipment to disrupt imported cells as described below); the power supply 18; the analog signal processor 42; and the digital processor 44, which includes the microcontroller 38 and the control logic implementer 46. Each of these four sections is discussed below, first with regard to data transmission and then with regard to control logic.

With regard to data transmission originating from the sensor cell 12, the sensor cell 12 provides current or voltage output that is proportional to the target species concentration. It is contemplated that the analog signal processor 42 receives signals from the sensor cell 12 through raw data line 48 and employs a current to voltage converter (not shown) and a programmable gain amplifier (not shown) to process the signals received. The digital output is then transmitted through digital data line 50 to the microprocessor 38, which then executes digital signal processing algorithms and formats data as needed. Output from the microcontroller 38 is contemplated to be transmitted through processed data line 52 to additional memory 54 as well as to an interface 56 to digital communications links.

With regard to the microprocessor's control function, the microprocessor 38 is contemplated to provide embedded instrument control, e.g., cell gating and electrode polarity comments, status monitoring, and other functions based upon the cell 10 and cell electronics 40 design. Toward this end, a control line 58 originating with the microprocessor serves to transmit control instructions to the control logic implementer 46, which in turn transmits control instructions to the cell specific electronics 40 and the analog signal processor 42 via control lines 60a and 60b, respectively. Thus, the microprocessor 38 controls the operations of the cell specific electronics section 40, which provides dedicated circuitry that is a function of the cell type. It is noted that electrical connection between the disposable sensor cell 12 and the remainder of the main body 22 of the sensor system 10 is provided by electrical connection 61.

With regard to the communication of data, it is contemplated that the microcontroller 38 would control the means by which the wearer of the sensor system 10 would be alerted, and that the sensor system 10 would include various means of communicating the presence of a target live microorganism. In the practice of the invention, the carrier of the sensor system 10 will preferably be alerted via some combination of an LED alarm 62, an LCD display 66, and a vibrating alarm and defeatable audible alarm heard through speaker 64, the latter two being similar in concept to that found in commercial personal pagers. In the embodiment depicted in FIG. 1, the alarm mechanism consists of an LED alarm indicator 62, an audible alarm produced by speaker 64, an LCD display 66. An LCD display might display such information as the type and level of biological warfare agent sensed along with pre-programmed instructions for the user to take given detection of the target live microorganism in his immediate area. It is noted that the alarm system employed is not limited to the examples disclosed herein; rather, any type of alarm system that fits within the confines of the sensor unit 10 and that is compatible with the other components therein may be employed.

It is also contemplated that the sensor unit 10 could be employed to relay information regarding the presence of a target live microorganism to remote locations. Specifically, radio links (not shown) and a global positioning satellite receivers (not shown) could be incorporated into the sensor unit 10 to automatically transmit results of analyses as well as the position of the sensor system 10 (i.e., precisely determined latitude and longitude) to a central computer system via satellite, orbiting aircraft, or directly via radio link. Additionally, a network of sensor systems could be employed, sans personnel, to relay such information without the risk of exposure to personnel.

Turning now to the components of sensor cell 12, at least one single-strand, modified oligonucleic sequence is provided therein that is capable of high rates of electron conductance when paired with its complementary sequence from a target live microorganism. To construct a modified oligonucleic sequence, one must first determine the sequence of a portion of the oligonucleic strand of a target live microorganism and then synthesize a complementary oligonucleotide sequence. The synthesized oligonucleotide sequence for a particular target live microorganism DNA may take many forms. For example, the complimentary target single stranded nucleic acid sequence may be contained within a larger nucleic acid sequence, i.e., all or part of a gene or mRNA, a restriction fragment of a plasmid or genomic DNA, among others. One skilled in the art of molecular biology would understand how to synthesize useful oligonucleotide sequences for use in the present invention. A separate oligonucleic sequence must be synthesized and modified for each target live agent of interest. One then covalently attaches electron donor and acceptor moieties at or near the opposing ends of the synthesized strand(s) using a technique such as disclosed by Meade et al.

More specifically, the termination of an oligonucleotide for use in the sensor cell 12 may be performed by (1) synthesizing an oligonucleotide sequence that is complementary to that of the target live agent DNA; (2) modifying the synthesized sequence with an amino-modified nucleotide, preferably terminal amino-ribose; (3) hybridizing the synthesized oligonucleotide sequence with a complementary sequence to form a double helix, thereby preventing the electron donor and electron acceptor precursors from attacking any and all bases in the sequence; (4) reacting the double helix with an electron donor moiety and an electron acceptor moiety such that the moieties are covalently attached to the modified synthesized sequence; and (5) removing the complementary sequence using standard methods from the synthesized, end-terminated oligonucleotide sequence. It is noted that the exposed amine or other ligand of the ribose (and other linkages) are readily modified with a variety of transition metal complexes with techniques readily known in the art.

The synthesized complementary oligonucleic sequence is affixed to an electrode in the sensor cell 12 of the sensor system 10. Although it would be possible to use known optical methods of detecting hybridization (as disclosed in Meade et al. 95/15971) which would not require an electrode, it is contemplated that the present sensor unit 10 will employ inexpensive and simple electrochemical characterization methods that employ an electrode component.

The sensor cell 12 may contain a single electrode or a plurality of electrodes, depending on the specificity of identification required. For example, a group of synthesized modified oligonucleotides, each one specific to different live microorganisms, may be affixed to the same electrode. In that instance, the presence of any one of the target live microorganisms would set off the sensor system.

Figures 4, 5, 6:
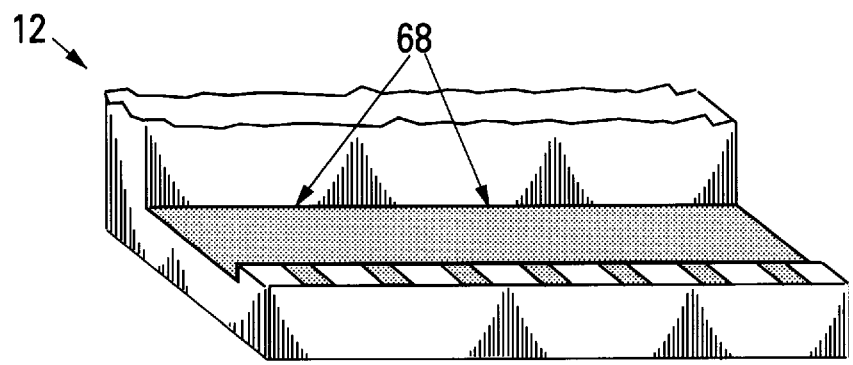
FIG. 4 is a schematic of a preferred embodiment of the internal components of the sensor cell of the sensor unit.
FIG. 5 depicts the general formula of a representative class of electron donors and acceptors.
FIG. 6 depicts a specific example of a ruthenium electron transfer donor moiety using bisbipyridine and imidazole as the ligands.

In the event that the sensor system 10 is used to identify a variety of target microorganisms, each of the synthesized modified oligonucleotides would be preferably affixed to a separate electrode, such that the sensor system would contain an array of electrodes, such as the linear array 68 of oligonucleotides/electrodes depicted in FIG. 4. In the embodiment of FIG. 4, the sensor system 10 would positively identify the specific target microorganism detected. The electrodes 30 of FIG. 4 would preferably be hooked in parallel through a switching diode array or other means (not shown) that allows each of the electrodes 30 to be cycled until a positive indication is observed. Once a positive indication occurs from an electrode 30, the switching array would be used in tandem with the microcontroller 38 to cycle each electrode individually until the one providing the positive indication is identified. It is contemplated that all of the electrodes in an array could be contained within the same electrolyte chamber, if electrochemical means are employed to measure the electron conductance.

With regard to improving identification of a particular target sequence, one may attach a plurality of identical sequences to a single electrode in order to increase the current flow to an easily measurable level. Additionally and preferably, the sensor system 10 is manufactured to offer independent confirmation of the detection of a target live microorganism. A plurality of oligonucleotides may be synthesized and modified that are complementary to different segments of the target live microorganism's DNA. Therefore, the presence of the target live microorganism is confirmed if portions of its DNA hybridize with a plurality of different synthesized sequences of oligonucleotides. In this fashion, false identification of a targeted sequence will be avoided, since hybridization of each of the synthesized sequences will be required for a positive identification of the targeted sequence.

It is contemplated that one end of the modified complementary sequence is attached to an electrode 30 via conductive polymers or fully conjugated hydrocarbon chains (such as polyacetylene or other rapid electron transfer species) that allow electron tunneling from the electrode, through the polymer, and into the electron donor or acceptor moiety at or near the end of the attached oligonucleotide.

Regarding the choice of conductive polymer, it is preferred that a redox polymer such as a poly-(vinylpyrridine) complex of $Os(bpy)_2Cl$ be cross-linked with an epoxide such as diepoxide to form a redox-conducting epoxide cement which is capable of strongly binding to electrodes made of conductive material such as gold, vitreous carbon, graphite, and other conductive materials. This strong attachment is included in the definition of "covalently attached" for the purposes of this embodiment. The epoxide cross-linking polymer is then reacted with, for example, an exposed amine, such as the amine of an amino-modified nucleic acid, covalently attaching the nucleic acid to the complex, forming a "redox hydrogel" on the surface of the electrode.

In the practice of the invention, sufficient opportunity should be provided for an imported target sequence to hybridize with the immobilized substituted oligonucleotide sequences inside the sensor cell 12. One way to separate individual substituted oligonucleotide sequences from one another is by providing an insulating layer therebetween. A nonexclusive example of a compound that may suitably serve as an insulating layer is a long chain alkyl thiol (not shown). Such insulators, which have been synthesized with various terminal groups including —H, —OH, and —COOH, also protect the internal electrical components of the sensor cell from oxidizing contaminants.

The DNA within a target live microorganism must be made accessible to the synthesized oligonucleotide attached to the electrodes of a sensor cell 12. Accordingly, it is necessary to disrupt the cell walls of the imported target live microorganism. This may be accomplished using a variety of known methods, among them being ultrasonic energy and other types of agitation, light energy, heat, and the activity of chemical species reduced into the electrolyte for this purpose. Preferably, chemicals are employed to disrupt the cell walls, with the chemicals being contained in the electrolyte solution and serving to degrade the cell wall or chemicals that enter the cell through its wall via osmosis, thereafter causing the cell wall to burst from accumulated pressure. Most preferably, the GeneReleaser®, which is commercially available from Bioventures, Inc., is employed in the practice of the invention. GeneReleaser® is a proprietary polymeric material that facilitates the release of DNA/RNA material from cells by lysing the cells treated with the GeneReleaser® using heat. The heat may be provided by heater elements contained in the cell specific electronics section 40.

With specific regard to the use of ultrasonic energy to disrupt the cell walls, an analogous use is that of ultrasonic "scalpels" that have been long used in surgical procedures. These instruments employ relatively low-energy ultrasonic waves to cut tissue. It is contemplated that the disruption of cell walls of single target microorganism cells will probably require a significantly lower energy level than that used in surgical instruments, although the same general principles obtain. One option is to mount the electrode 30 to which the synthesized oligonucleic acid is attached directly on top of the ultrasonic transducer (not shown) and apply a small amount of ultrasonic energy directly through the electrode to the absorbed live microorganism. Employing ultrasonic energy to disrupt the cell walls is advantageous in that minimal energy would be required from the battery for periodic pulses of such energy, therefore reducing the size of the battery required and the associated capacity for power and heat dissipation in the ultrasonic transducer. An additional benefit of employing ultrasonic energy would be the resultant mixing of the electrolyte, which would then hasten the hybridization process between the synthesized oligonucleotide and the target live DNA.

Other options for disrupting the cell walls of the target live DNA include the use of light energy, specifically ultraviolet or blue visible light as directed by light pipes or optical fibers to the absorbed microorganism. In the case of blue light, possible light sources would include a laser diode or LED.

When the target live agent DNA is imported into the sensor cell 12 through an inlet port 14, a portion of its DNA will hybridize with the synthesized oligonucleotide, which is end-terminated or near-end-terminated with both an electron donor moiety and acceptor moiety, thereby forming the characteristic double helix structure. It is a characteristic of this π-bonded structure that there is extensive electron delocalization between the two strands, such that electron transfer up and down the center of the double helix is very rapid, on the order of 10,000-fold more rapid than electron transfer along either of the single strands making up the double helix. The delocalized electron cloud between the strands serves to establish a conductive path between the electron donor moiety and the electron acceptor moiety that behaves, in effect, like a "wire". If the specific live agent is not present, the oligonucleotide will be a single strand and, as the voltage cycles from positive, through zero, to negative, and through zero again, very little current will flow in the molecule. On the other hand, if a live agent is present with DNA containing a section whose base sequence is complementary to that of the oligonucleotide, the double helix will form, and a significant current will flow into and out of the oligonucleotides.

The electron transfer rate into and out of the oligonucleotide depends upon several factors, including the distance between the electron donor-acceptor pair, the free energy ($\Delta G$) of the reaction, the reorganization energy ($\lambda$), the contribution of the intervening medium, the orientation and electronic coupling of the donor and acceptor pair, and the hydrogen bonding between the bases. The latter confers a dependence on the actual nucleic acid sequence, since adenine-thymidine (A-T) pairs contain one less hydrogen bond than cytosine-guanine (C-G) pairs. However, this sequence dependence is overshadowed by the determination that there is a measurable difference between the rate of electron transfer within a DNA base-pair matrix, and the rate through the ribose-phosphate backbone, the solvent, or other electron tunnels. The rate differential is thought to be at least several orders of magnitude, and may be as high as four orders of magnitude greater through the stacked nucleotide bases as compared to other electron transfer pathways.

Regarding the dependence of the rate of electron conductance on the nucleotide distance between the electron donor and acceptor moieties, it is axiomatic that longer distances will exhibit slower rates. Therefore, consideration of the rate of electron conductance will necessarily be a parameter in the design of the sensor system. While it is possible to measure rates for distances in excess of 100 nucleotides, a preferred embodiment has the electron donor moiety and the electron acceptor moiety separated by at least 3 and not more than 100 nucleotides. More preferably, the moieties are separated by 8 to 64 nucleotides, with 15 being the most preferred.

Preferably, the electron donor and acceptor moieties are placed at or near the end of the synthesized oligonucleic acid strand. As such, the electron donor and acceptor moieties may be added to the 3' and/or 5' termini of the nucleic acid. While not preferred, the electron donor and acceptor moieties may also be added to the backbone of one or more internal nucleotides, that is, any nucleotide which is not the 3' or 5' terminal nucleotide. Further, the electron transfer moieties may also be added to the backbone of both internal and terminal nucleotides in any combination. The techniques by which the addition of moieties to various positions along the oligonucleotide backbone may be achieved are described in the publications of Meade et al cited above.

Notably, the manner by which the electrical conductance of the nucleic acid is measured will be a factor in the distance employed between the electron donor and acceptor moieties. More specifically, the longer the synthesized oligonucleotide, the greater its resistance to electron transfer, such that more double helixes are required to generate the same signal intensity. Thus, while the specificity of a synthesized oligonucleotide is increased with the number of bases employed, the resulting signal generated may be too low for detection by certain detection systems. Preferably, no more than about twenty bases are employed in a single substituted oligonucleotide. For a relatively long target sequence, one may boost signal intensity by employing several different oligonucleotides coded for different portions of the same target sequence, as described above. For example, if a fifty-base sequence is required for unambiguous identification of a target sequence, one may employ four fourteen-base oligonucleotides each attached to different electrodes, such that signal intensities are increased and higher specificity is maintained.

Thus, in addition to affecting signal intensity, the length of the synthesized oligonucleotide affects the degree of accuracy in identifying a particular target sequence. As is known in the art, there are five possible base types available for synthesis of an oligonucleotide sequence: guanine, cytosine, adenine, thymidine, and uracil. Therefore, the odds against random replication of a specific string of three bases would be 125:1, while the odds against random replication of a specific string of fifteen bases would be about 30,000,000:1. Therefore, the accuracy of an oligonucleotide sequence is directly proportional to the number of bases it comprises. Preferably, an oligonucleotide having about fifteen bases is employed. It is noted that while hybridization may still occur between a synthesized oligonucleotide and a target sequence even if each base is not complementary, the base mismatch will inject a "resistor" in the hybridized electron transfer path and would therefore greatly reduce electron transfer.

Regarding the types of electron donor and acceptors that may be employed in the practice of the invention, a general formula representative of a class of donors and acceptors that may be employed is shown in FIG. 5. In this figure, M may be Cd, Mg, Cu, Co, Pd, An, Fe, or Ru, to name a few, with the most preferred being ferrocene and ruthenium. Of the two preferred species, ruthenium is more familiar for these purposes but it has been discovered that ferrocene has a significant advantage: ferrocene oxidizes at +400 mV (versus saturated calomel electrode), making ferrocene convenient for electrochemical analysis in aqueous solutions that would hydrolyze at the high potentials required for ruthenium complex moieties. The groups $R^1$, $R^2$, $R^3$, $R^4$, and $R^5$ may be any coordinating ligand that is capable of covalently binding to the chosen metal and may include ligands such as $NH_3$, pyridine, isonicotinamide, imidazole, bipyridine, and substituted derivatives of bipyridine, phenanthrolines, and substituted derivatives of phenanthrolines, porphyrins, and substituted derivatives of the porphyrin family. The structure of a ruthenium electron transfer species using bisbipyridine and imidazole as the ligands is shown in FIG. 6. Specific examples of useful ruthenium electron transfer complexes include, but are not limited to, those shown in Table I:

TABLE I

Examples of Electron Transfer Complexes.

| Electron Transfer Donors | Electron Transfer Acceptors |
|---|---|
| Ru(bpy)$_2$im-NH$_2$-U | Ru(NH$_3$)$_5$-NH$_2$-U |
| Ru(bpy)$_2$im-NH$_2$-U | Ru(NH$_3$)$_4$py-NH$_2$-U |
| Ru(bpy)$_2$im-NH$_2$-U | Ru(NH$_3$)$_4$im-NH$_2$-U | where Ru = ruthenium
bpy = bisbipyridine
im = imidazole
py = pyridine

It will be understood that the number of possible donor moieties and electron acceptor moieties is very large, and that one having ordinary skill in the art of electron transfer compounds will be able to use a number of compounds in the present invention. The preferred formulations for donors and acceptors will possess a transition metal covalently attached to a series of ligands, as described above, and further covalently attached to an amine group as part of the ribose ring (2' or 3' position) of to a nitrogen or sulfur atom as part of a nucleotide dimer linked by a peptide bond, phosphoramidate bond, phosphorothioate bond, phosphorodithioate bond or O-methyl phosphoramidate bond.

An acceptable and already demonstrated electron donor moiety is 5'-2'-ruthenium bisbipyridineimidazoleamineouridine, which is attached to the deoxyribose backbone via the ribose moiety of the uridine. An acceptable electron acceptor moiety are 5'-2'-ruthenium tetraaminepyri-dineaminouridine, or 5'-2'-ruthenium tetraamineimidazoleaminouridine, or 5'-2'-ruthenium pentaamineaminouridine, or other similar species. Notably, different species of electron donor and acceptor moieties may be attached to a single stranded nucleic acid.

All told, the present sensor unit 10 offers real-time detection of harmful microorganisms that is both highly sensitive and highly selective. Further, it is easily adaptable for field use, including both air and water sampling, given that it is small and lightweight. Specifically, it is contemplated that the entire system body 22 will be about the size of a pack of cigarettes. The casing which contains the elements of the sensor system may be made of any sufficiently rigid material, such as a lightweight plastic. The sensor unit 10 is also relatively inexpensive to produce and operate. Thus, the present sensor unit 10 represents an optimal solution to the problem of real-time detection of BWA's in field operations.

Thus, there has been disclosed a sensor system for the real-time detection of target live microorganisms as well as a method of detecting in real time such microorganisms and a method of making the sensor system. It will be readily apparent to those skilled in the art that various changes and modifications of an obvious nature may be made without departing from the spirit of the invention, and all such changes and modifications are considered to fall within the scope of the invention as defined by the appended claims.

What is claimed is:

1. A sensor system capable of detecting target live microorganisms in real time in a fluid environment, said sensor system being immersed in said fluid environment such that said sensor system is surrounded by said fluid environment, each of said target live microorganisms having unique nucleic acid, a portion of which, as a single strand, represents a target sequence of nucleotides, said sensor system comprising:

A. a first assembly comprising:
   (a) a sensor cell in the form of a replaceable cartridge and comprising:
      (i) at least one electrode, and
      (ii) at least one single-stranded oligonucleic acid in electrical communication with said at least one electrode, said at least one single-stranded oligonucleic acid being complementary to said target sequence of nucleotides and therefore capable of hybridizing therewith to form a hybridization complex, said at least one single-stranded oligonucleic acid containing at least one electron donor moiety and at least one electron acceptor moiety, said electron donor moiety and said electron acceptor moiety being covalently attached to said at least one single-stranded oligonucleic acid, said sensor cell having an outer casing that defines an internal volume of said sensor cell;
   (b) at least one inlet port defined by said outer casing, said at least one inlet port allowing fluidic communication between said fluid environment surrounding said sensor system and said internal volume of said sensor cell, such that fluid from said fluid environment may be imported into said sensor cell, said fluid including cells having cell walls encapsulating nucleic acid;
   (c) a cell wall disrupter to lyse said cell walls such that said encapsulated nucleic acid is released into said internal volume of said sensor cell;
   (d) an electron transfer rate measuring system for measuring the electron transfer rate through said at least one single-stranded oligonucleic acid, said single-stranded oligonucleic acid exhibiting a base electron transfer rate in the absence of said target sequence of nucleotides and an increased electron transfer rate in the presence of said target sequence, having formed said hybridization complex wherein said electron transfer rate measuring system initiates electron transfer by a mechanism selected from the group consisting of cyclic voltammetry, pulse polarography, and impedance measurements;
   (e) a microcontroller to compare said measured electron transfer rate with said base electron transfer rate to determine the presence or absence of said target sequence of nucleotides in said fluid; and
   (f) a communication system for relaying information regarding said presence or absence of said target sequence of nucleotides in said fluid environment surrounding said sensor system to a user of said sensor system; and B. a second assembly comprising:
   (a) a power source for supplying power to operate said sensor system; and
   (b) a pump powered by said power source to import a fluid sample from said fluid environment surrounding said sensor system into said sensor cell through said at least one inlet port, wherein said first assembly and said second assembly are capable of fluidically and electrically communicating therebetween.

2. The sensor system of claim 1 wherein said sensor cell comprises a plurality of single-stranded oligonucleic acids that are complementary to a plurality of target sequences of nucleotides.

3. The sensor system of claim 2 wherein said sensor cell comprises as many electrodes as target sequences of nucleotides.

4. The sensor system of claim 2 wherein said sensor cell comprises a single electrode.

5. The sensor system of claim 1 wherein said at least one electrode is placed in a gelled electrolyte within said sensor cell and wherein said at least one single-stranded oligonucleic acid is affixed to said at least one electrode by means of a conductive polymer.

6. The sensor system of claim 1 wherein said sensor cell further comprises at least one insulating layer between each said at least one single-stranded oligonucleic acid.

7. The sensor system of claim 5 wherein said cell wall disrupter is selected from the group consisting of ultrasonic energy, light energy, thermal energy, and activity of a chemical species reduced into said electrolyte.

8. The sensor system of claim 7 wherein said cell wall disrupter is a chemical species reduced into the said electrolyte capable of causing said cell wall to rupture given immersion of said cell in said electrolyte.

9. The sensor system of claim 1 wherein said at least one single-stranded oligonucleic acid comprises about fifteen base nucleotides between said at least one electron donor moiety and said at least one electron acceptor moiety.

10. The sensor system of claim 1 wherein said at least one electron donor moiety and said at least one electron acceptor moiety are covalently attached to the ribose-phosphate backbone of said at least one single-stranded oligonucleic acid.

11. The sensor system of claim 1 wherein said at least one electron donor moiety and said at least one electron acceptor moiety are metal complexes selected from the group consisting of ruthenium metal complexes and ferrocene metal complexes.

12. The sensor system of claim 11 wherein said at least one electron donor moiety is selected from the group consisting of 5'-2'-ruthenium bisbipyridineimidazoleaminoeuridine and derivatives thereof and wherein said at least one electron acceptor moiety is selected from the group consisting of 5'-2'-ruthenium tetraaminepyridineaminouridine, 5'-2'-ruthenium tetraamineimidazoleaminouridine, 5'-2'-ruthenium pentaamineaminouridine, and derivatives thereof.

13. The sensor system of claim 1 wherein said communication system comprises at least one component selected from the group consisting of a liquid crystal display, an audible alarm, a vibrating alarm, an LED alarm indicator, and a radio link.

* * * * *